United States Patent [19]
Hofmann

[11] Patent Number: 5,501,662
[45] Date of Patent: Mar. 26, 1996

[54] IMPLANTABLE ELECTROPORATION METHOD AND APPARATUS FOR DRUG AND GENE DELIVERY

[75] Inventor: Gunter A. Hofmann, San Diego, Calif.

[73] Assignee: Genetronics, Inc., San Diego, Calif.

[21] Appl. No.: 304,584

[22] Filed: Sep. 12, 1994

Related U.S. Application Data

[63] Continuation-in-part of Ser. No. 887,315, May 22, 1992, abandoned.

[51] Int. Cl.$^6$ .................................................. A61N 1/30
[52] U.S. Cl. .............................. 604/20; 604/41; 607/116; 435/173.6
[58] Field of Search .................... 600/1, 2, 13, 14; 604/890.1, 891.1, 892.1, 20, 21, 49, 52, 53; 435/172.2, 173.6, 287, 289; 204/180.1, 299 R; 935/52; 128/639, 642, 644; 607/1-3, 65, 72, 74, 98-101, 113, 115, 116, 117, 144-145, 154-156

[56] References Cited

U.S. PATENT DOCUMENTS

| | | | |
|---|---|---|---|
| 2,320,462 | 6/1943 | Nawells | 607/145 |
| 3,978,864 | 9/1976 | Smith et al. | 607/155 |
| 4,400,178 | 4/1984 | Bussard et al. | 607/121 |
| 4,639,244 | 1/1987 | Rizk et al. | 604/891.1 |
| 4,690,130 | 9/1987 | Mirell | 600/2 |
| 4,801,459 | 1/1989 | Liburdy | 600/2 |
| 4,842,598 | 6/1989 | Tran | 604/891.1 |
| 4,906,576 | 3/1990 | Marshall, III | 435/287 |
| 4,936,317 | 6/1990 | MacGregor | 607/120 |
| 4,970,154 | 11/1990 | Chang | 453/172.2 |
| 5,016,615 | 5/1991 | Driller et al. | 604/891.1 |
| 5,019,034 | 5/1991 | Weaver et al. | 604/890.1 |
| 5,042,975 | 8/1991 | Chien et al. | 604/20 |
| 5,087,243 | 2/1992 | Auitall | 607/120 |
| 5,183,456 | 2/1993 | Liboff et al. | 600/13 |
| 5,236,413 | 8/1993 | Feiring | 607/116 |
| 5,246,437 | 9/1993 | Abela | 604/21 |
| 5,273,525 | 12/1993 | Hofmann | 604/21 |
| 5,286,254 | 2/1994 | Shapland et al. | 604/21 |
| 5,290,409 | 3/1994 | Liboff et al. | 600/13 |
| 5,304,120 | 4/1994 | Crandell et al. | 604/21 |
| 5,318,514 | 6/1994 | Hofmann | 604/20 |
| 5,389,069 | 2/1995 | Weaver | 604/21 |
| 5,439,440 | 8/1995 | Hofmann | 604/20 |

FOREIGN PATENT DOCUMENTS

| | | | |
|---|---|---|---|
| 686287 | 3/1965 | Italy | 607/145 |
| 0024640 | 9/1978 | U.S.S.R. | 604/20 |
| 8910690 | 11/1989 | WIPO | 604/20 |

OTHER PUBLICATIONS

Engineering Circuit Analysis, 3rd Ed. pp. 136–137, 526–529.
Modern Dictionary of Electronics, pp. 156, 242.

Primary Examiner—Randall Green
Assistant Examiner—K. M. Reichle
Attorney, Agent, or Firm—Baker, Maxham, Jester & Meador

[57] ABSTRACT

A method and apparatus are provided for introducing molecules such as genes and pharmacological compounds into living blood cells of a patient for therapeutic purposes. A device is implanted into the body of the patient for generating an electric field at a preselected location within a selected blood vessel. Preselected molecules are infused into the selected blood vessel. Simultaneously an electric signal is applied to the implanted device to repeatedly subject a quantity of blood flowing within the selected blood vessel past the preselected location to electric fields of a predetermined amplitude and duration. The parameters of the electric fields are precisely controlled in order to make the walls of preselected cells in the blood transiently permeable to permit the molecules to enter said preselected cells without killing said cells. The device can include either a pair of electrodes implanted in the blood vessel, or alternatively, an induction coil that surrounds the blood vessel. The electric signal is supplied by a power pack and the preselected molecules are infused with a supply pump.

20 Claims, 5 Drawing Sheets

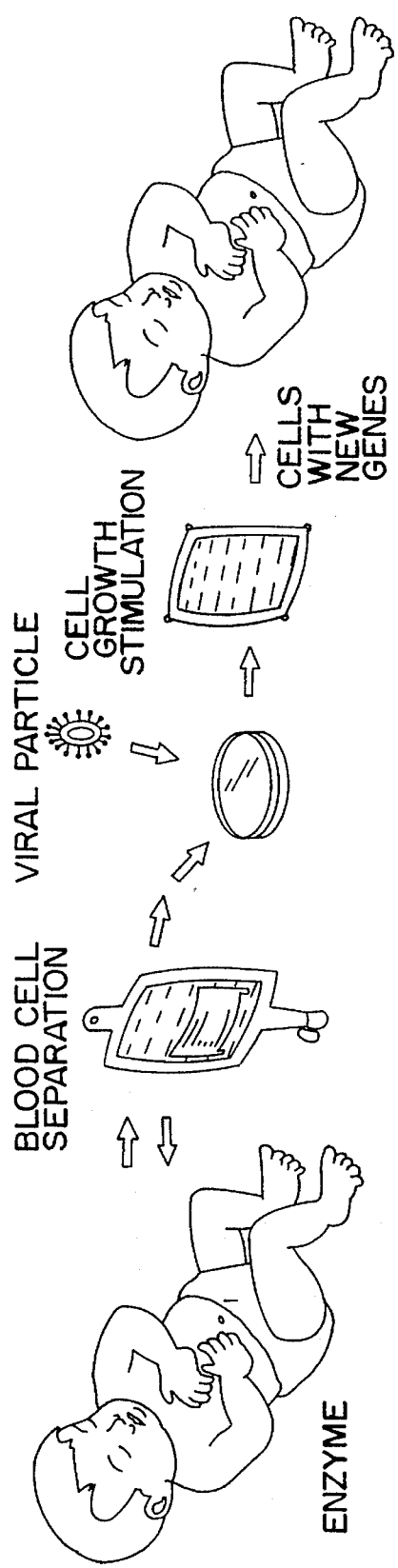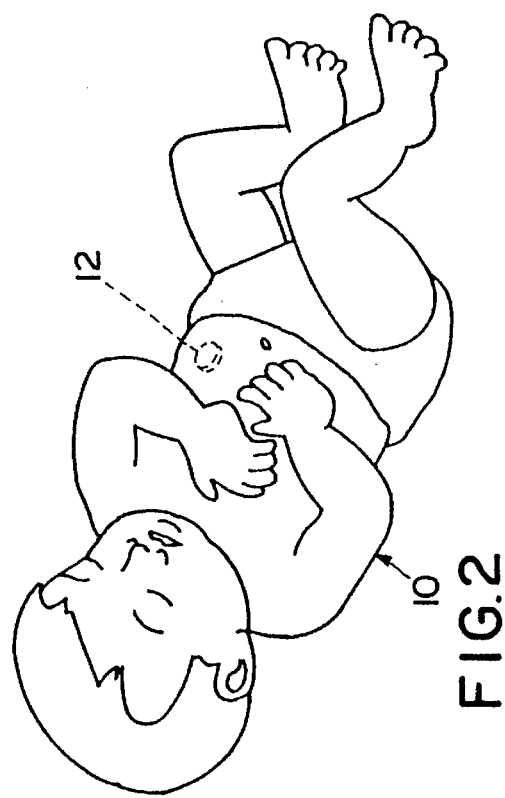

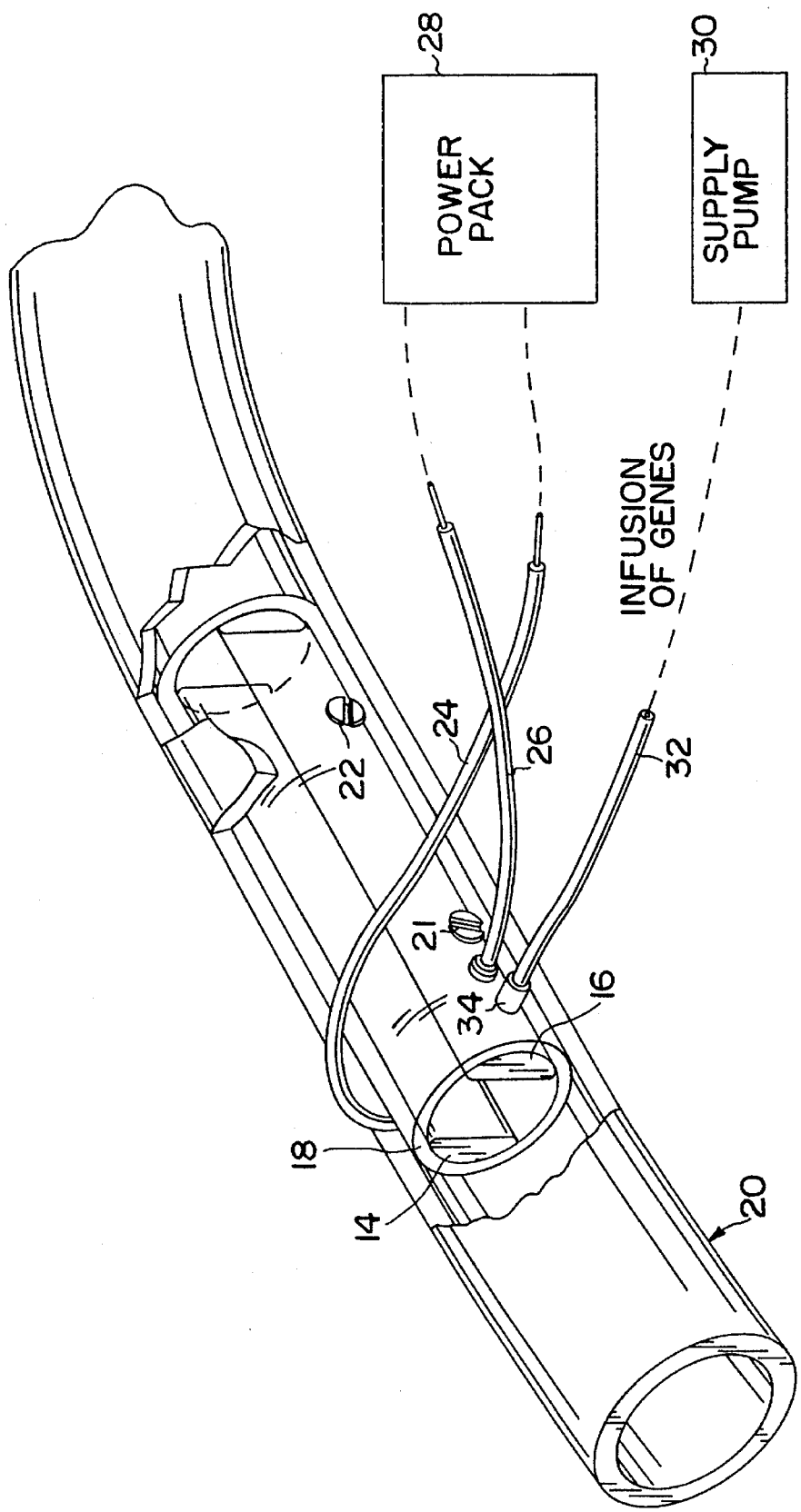

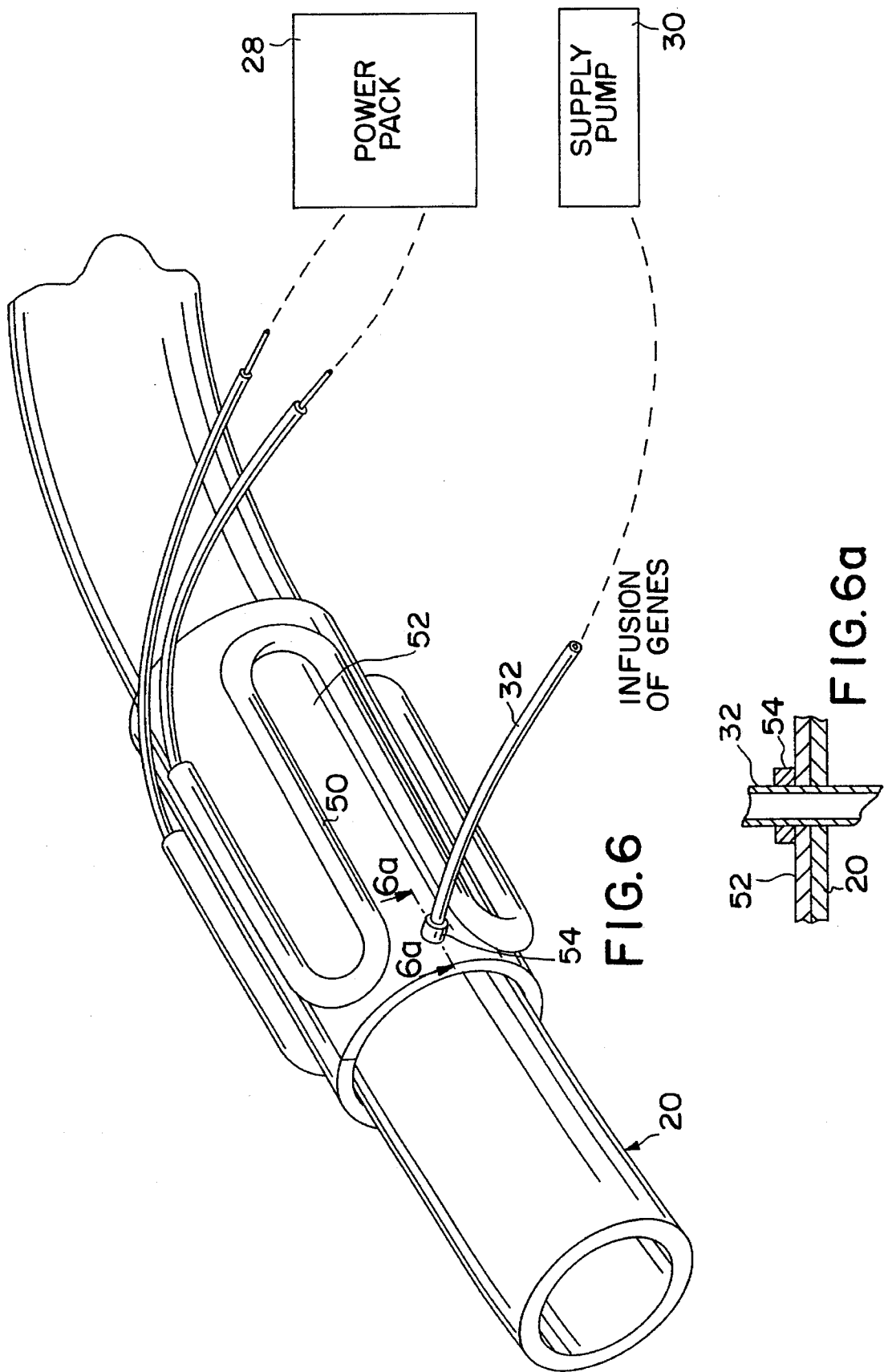

IMPLANTABLE ELECTROPORATION METHOD AND APPARATUS FOR DRUG AND GENE DELIVERY

REFERENCE TO RELATED APPLICATION

This is a continuation-in-part of U.S. patent application Ser. No. 07/887,315, filed May 22, 1992, entitled "Implantable Electroporation Method and Apparatus for Drug and Gene Delivery", now abandoned.

BACKGROUND OF THE INVENTION

The present invention relates to the treatment of ailments in humans and other mammals, and more particularly, to a method and apparatus for delivering pharmaceutical compounds and genes into live cells of a patient.

It has long been known that it would be desirable to target certain cells within the body with specific pharmaceutical compounds. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

Similarly, certain diseases could be treated by introducing desired genes into the specific cells of the patient. At present, most gene therapy experiments have utilized retroviruses as the carrier of the gene into the cells. When a retrovirus enters a target cell, it integrates essentially randomly in the genome and thus has the potential for introducing mutational damage by the mere fact of its insertion. If the virus integrates adjacent to an oncogene, malignant transformation of the target cell can result.

It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells. There they can modify the genome of the cell.

The incorporation of drugs into red blood cells via electroporation as well as the incorporation of genes into white blood cells via electroporation have both been demonstrated. The selective incorporation of genes into white blood cells in whole blood via electroporation has also been demonstrated. The electroporation of cells in a flow-through apparatus has also been demonstrated.

Recent methods of gene therapy have used the procedure illustrated in FIG. 1. A substantial amount (e.g. 10%) of a patient's blood is withdrawn and the red and white blood cells are separated over a lengthy time period (e.g. four hours). The red blood cells are then re-infused. A new gene is inserted into the separated white blood cells utilizing a retrovirus. The growth of the white cells is then stimulated before they are re-infused into the patient. The procedure must be repeated every few months and the costs can reach $100,000.00 annually.

It would be desirable to eliminate the need for separating the white cells from the red blood cells. This in turn would eliminate the need to withdraw and re-infuse a portion of the patient's blood. This would make it more convenient and less expensive to perform gene therapy on living patients by genetically modifying their lymphocytes. It would also make it more convenient and less expense to deliver drugs to selected tissues and organs of a living human body by encapsulating them into red blood cells. It would also be desirable to eliminate the need to utilize retroviruses which can result in malignant transformation of the target cells.

SUMMARY OF THE INVENTION

Accordingly, it is the primary object of the present invention to provide an improved method of electroporation mediated, in vivo, intracellular drug and gene delivery for a living patient.

It is another principal object of the present invention to provide an improved apparatus for electroporation mediated, in vivo, intracellular drug and gene delivery.

The invention provides a useful method and apparatus for introducing molecules such as genes and pharmacological compounds into living blood cells of a patient for therapeutic purposes. A device is implanted into the body of the patient for generating an electric field at a preselected location within a selected blood vessel. Preselected molecules are infused into the selected blood vessel. Simultaneously an electric signal is applied to the implanted device to repeatedly subject a quantity of blood flowing within the selected blood vessel past the preselected location to electric fields of a predetermined amplitude and duration. The parmeters of the electric fields are precisely controlled in order to make the walls of preselected cells in the blood transiently permeable to permit the molecules to enter said preselected cells without killing said cells. The device can include either a pair of electrodes implanted in the blood vessel, or alternatively, an induction coil that surrounds the blood vessel. The electric signal is supplied by a power pack and the preselected molecules are infused with a supply pump.

BRIEF DESCRIPTION OF THE DRAWINGS

FIG. 1 illustrates a prior art approach to gene therapy which employs retroviruses.

FIG. 2 illustrates a patient with a device implanted in his body for effecting in vivo electroporation of molecules into blood cells in one of his blood vessels in accordance with the present invention.

FIGS. 3–6 are enlarged perspective views of alternative embodiments of the apparatus for effecting in vivo electroporation of molecules into a blood vessel. The power pack and supply pump components of the apparatus are illustrated in block diagram form. Throughout FIGS. 3–6 like reference numerals refer to like parts.

FIG. 6a is a section view taken on line 6—6 of FIG. 6.

DETAILED DESCRIPTION OF THE PREFERRED EMBODIMENTS

Figure 4:
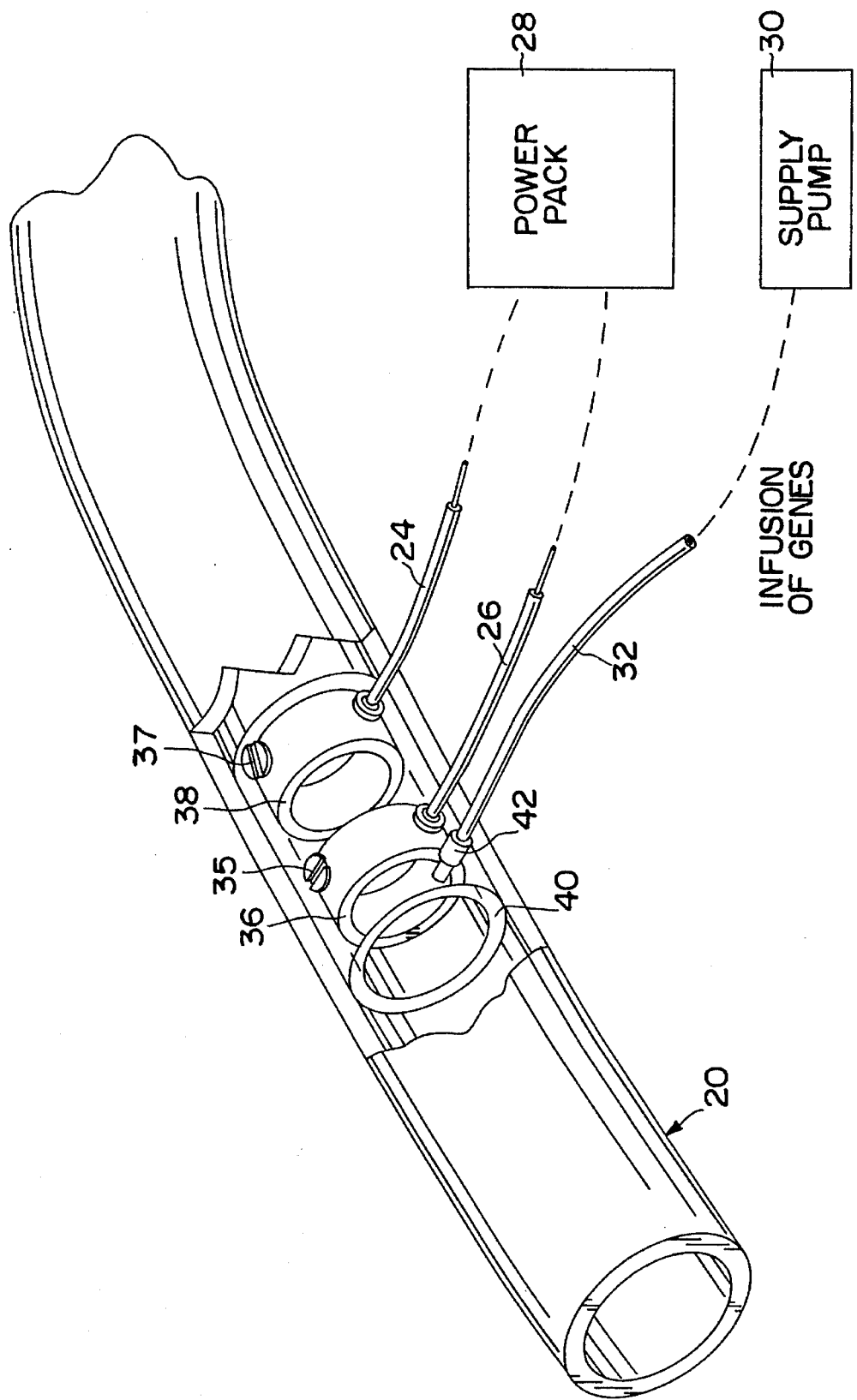

As used herein the term "molecules" includes pharmacological agents, genes, antibodies or other proteins. Referring to FIG. 2, the preferred embodiment of my apparatus includes a device 12 which is implanted in a patient 10 for repeatedly generating electric fields of a predetermined amplitude and duration. The fields are generated by applying a predetermined electric signal to the device. The parameters of the signal are selected so that a quantity of blood flowing within the selected blood vessel is subjected to short pulses of high intensity electric fields. These fields make the walls of preselected cells in the blood transiently permeable to permit the molecules to enter said preselected cells without killing said cells. The permeability results from the temporary formation of pores in the cells walls which are large enough to permit migration of the molecules through the cell walls.

A first embodiment of an implantable electric field generating device is illustrated in FIG. 3. It includes a pair of spaced apart split cylinder conductive electrodes 14 and 16 mounted within a cylindrical dielectric carrier 18. The diametrically spaced electrodes 14 and 16 present opposing planar surfaces and are preferably made of stainless steel. The electrodes are positioned around the center of the blood vessel a predetermined uniform distance apart and from the center of the vessel so that the flowing blood passes between them. They are preferably positioned so that the electric field generated by them is located at the center of the blood vessel. The carrier 18 is a dielectric cylinder and may be made of a suitable material such as a synthetic resin polymer such as that sold under the trademark "TEFLON" so that the carrier can be surgically implanted within a surrounding blood vessel 20 with minimal complications from blood clotting. The electrodes 14 and 16 are also preferably coated with a semipermeable layer to impede localized blood clotting. The resin polymer material, e.g., "TEFLON" has pores which are too small to permit blood cells to pass through the same, but the pores are large enough for ions to carry the electroporation current.

The ends of the electrodes 14 and 16 may be releasably secured to the carrier via screws such as 21 and 22. The electrodes 14 and 16 are connected via wires 24 and 26 to a power pack 28 which includes a signal generator. This power pack is preferably mounted outside the patient's body with the wires 24 and 26 extending subcutaneously. A supply pump 30 is connected through a very small diameter tubing segment 32 to a fitting 34. This fitting is mounted in a hole through the electrode 16 and opens into the space between the electrodes to deliver fluid through the electrode 16 to the space between electrode 14 and 16. The supply pump is also preferably mounted outside the patient's body.

The supply pump 30 (FIG. 3) delivers a fluid medium carrying preselected molecules such as genes or pharmacological compounds for introduction into the blood vessel adjacent the electrodes 14 and 16 which generate the electric fields necessary for electroporation. The supply pump 30 may be of the conventional type that employs a syringe (not illustrated) for holding a predetermined quantity of the fluid medium. Where genes are to be infused into the patient, the fluid medium is selected so that it will support the viability of the genes until they are inserted into the blood cells of the patient. Such fluid mediums are well known to those skilled in the art. The plunger of the syringe may be pushed inwardly by a motor driven piston assembly (not illustrated). The rate of delivery of the fluid medium from the syringe through the tubing segment 32 may be manually adjusted via controls with the delivery parameters being indicated on a display.

The function of the signal generator in the power pack 28 (FIG. 3) is to generate a predetermined electric signal which, when applied to the electrodes 14 and 16 results in applying electric fields of a predetermined amplitude and duration to the blood flowing therethrough the blood vessel 20. Preferably these fields are applied repeatedly and their amplitude and duration make the walls of preselected cells in the blood sufficiently permeable to permit the molecules to enter the preselected cells without killing them.

One suitable signal generator is the ELECTRO CELL MANIPULATOR Model ECM 600R commercially available from GENETRONICS, INC. of San Diego, Calif., U.S.A. The ECM 600R signal generator generates a pulse from the complete discharge of a capacitor which results in an exponentially decaying waveform. The electric signal generated by the ECM 600R signal generator is characterized by a fast rise time and an exponential tail. In the ECM 600R signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads).

The passage of an electrical current across the cell membrane results in the creation of transient pores which are critical to the electroporation process. The ECM 600R signal generator provides the voltage (in kV) that travels across the gap (in cm) between the electrodes 14 and 16. This potential difference defines what is called the electric field strength where E equal kV/cm. Each cell species has its own critical field strength for optimum electroporation. This is due to cell size, membrane make-up and individual characteristics of the cell wall itself. For example, some Gram positive bacteria are quite resistant to electroporation and require very high field strengths, i.e., greater than 17 kV/cm, before cell death and/or electroporation occurs. Generally, the required field strength varies inversely to the size of the cell.

The ECM 600R signal generator has a knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600R signal generator. This device further includes a plurality of push button switches for controlling pulse length, in the Low VM mode, by a simultaneous combination of resistors parallel to the output and a bank of seven selectable additive capacitors.

The ECM 600R signal generator also includes a single automatic charge and pulse push button. This button may be depressed to initiate both charging of the internal capacitors to the set voltage and to deliver a pulse to the flow-through chamber is an automatic cycle that takes less than five seconds. The manual button may be sequentially pressed to repeatedly apply the predetermined electric field to the mixture of blood and fluid medium or a repetitive charge/pulse mode may be selected with an adjustable repetition rate.

By selecting the electrical parameters of the pulses, a preferred encapsulation into one of the different blood cell types is possible. If it is desirable to encapsulate drugs than one would preferably choose red blood cells as the target cells. If a gene is to be encapsulated, e.g for gene therapy purposes, one would preferably choose white blood cells as target cells. The infused genes can then recombine with the genome of the white blood cells to alter their properties.

The waveforms of the electrical signal provided by the signal generator in the power pack 28 can be an exponentially decaying pulse, a square pulse, a unipolar oscillating pulse train or a bipolar oscillating pulse train. The electric field strength can be 0.2 kV/cm to 20 kV/cm. The pulse length can be ten microseconds to one hundred milliseconds. There can be one to one hundred pulses per liquid volume element as it passes through the blood vessel 20. Of course the waveform, electric field strength and pulse duration are dependent upon the type of cells and the type of molecules that are to enter the cells via electroporation. In one application for example, the preselected cells are lymphocytes, the electric field has a strength of approximately 0.55 kV/cm and the signal has a pulse train wave form that decays exponentially with a pulse duration of approximately fifty to fifty-five milliseconds.

FIG. 4 illustrates an alternate embodiment of the implantable electric field generating device which includes resin polymer material, e.g., "TEFLON", coated stainless steel ring-shaped electrodes 36 and 38. The ring-shaped electrodes 36 and 38 are mounted such as by means of screws 35 and 37 in axially spaced configuration inside a polymer dielectric cylinder 40. A fitting 42 is mounted in a hole extending through the cylinder 40 so that tube 32 opens into the blood stream upstream of the electrodes. The remaining parts of the apparatus illustrate in FIG. 4 are similar to those illustrated in the apparatus of FIG. 3 and are labeled with like reference numerals. This arrangement also positions the electrodes uniformly around and from the center of the blood vessel so that blood flows between the electrodes as in the prior embodiment. This centers the electric field at the center of the blood vessel.

Figure 5:
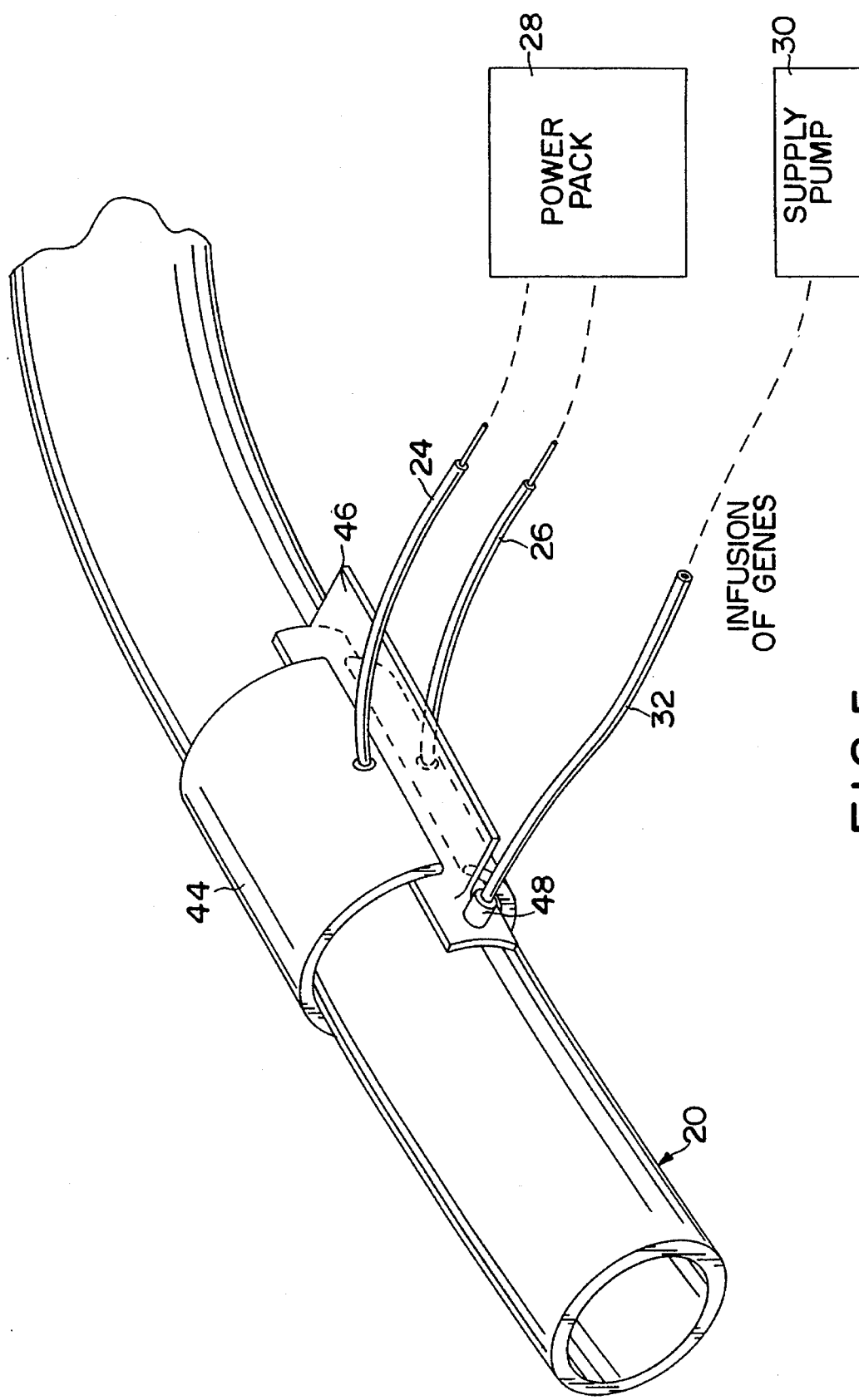

In an alternate implementation of my method, the electric field inside the blood vessel 20 is generated by an induction coil surrounding the blood vessel. While induction coils are not considered the equivalent of electrodes, they can be used in the present environment to generate suitable electric fields. Referring to FIG. 5, a flexible single turn coil 44 surrounds the blood vessel 20. This coil is in the form of a split cylinder of pliant metal. The split edges of the coil 44 engage and are separated by an elongate insulator 46 made of a dielectric material. The insulator 46 has a T-shaped cross-section and has a fitting 48 for connection to the tubing segment 32. The tubing segment 32 preferably has a spike tip as shown in FIG. 6a to extend through the blood vessel and deliver the molecule carrying fluid directly into the blood stream upstream of the electric field. The advantage of this configuration of the implantable device over those of FIGS. 3 and 4 is that the blood vessels are not invaded and it completely avoids the blood clotting problem. It may also avoid some of the conduction problems.

Another non-contact embodiment of implantable electric field generating device is illustrated in FIG. 6. It includes a serpentine coil 50 wound along a split dielectric cylinder 52 having a fitting 54. The dielectric cylinder can be expanded to be fit around the blood vessel 20. The infusion supply line as shown in FIG. 6a is connected by a fitting 54 and it has a suitable tip such as a spike as in the prior embodiment to deliver the fluid directly into the blood stream.

In all embodiments of the present invention the implantable field generating device is implanted in or around the blood vessel in close proximity (less than the diameter of the blood vessel) to the blood stream. This reduces the length of conductive paths for the electric signals. The term "close proximity" as used herein means a distance of less than the diameter of the blood vessel.

While I have described preferred embodiments of my implantable electroporation method and apparatus for drug and gene delivery, it should be understood that modifications and adaptations thereof will occur to persons skilled in the art. For example, the power pack and pump could also be implanted inside the patient's body. Therefore, the protection afforded my invention should only be limited in accordance with the scope of the following claims.

I claim:

1. A method of introducing molecules into living blood cells of a patient for therapeutic purposes, comprising the steps of:

providing an implantable electric field generating device;

implanting said device into a body of the patient at a preselected location within close proximity of a selected blood stream and disposed at least partially around a center of a selected blood vessel through which the selected blood stream flows for generating electric fields at a preselected location within said selected blood vessel;

infusing preselected of said molecules into the selected blood vessel upstream of the preselected location within said selected blood vessel; and applying an electric signal to the implanted device to cause it to generate electric fields of a predetermined amplitude and duration to repeatedly subject a quantity of blood flowing past the preselected location within the selected blood vessel to said electric fields of a predetermined amplitude and duration in order to make the walls of preselected cells in the blood transiently permeable to permit the molecules to enter said preselected cells without killing said cells.

2. A method according to claim 1 wherein the molecules are selected from the group consisting of genes and pharmacological compounds.

3. A method according to claim 1 wherein the preselected cells are selected from the group consisting of red and white blood cells.

4. A method according to claim 1 wherein the device for generating the electric fields includes a paid pair of spaced apart electrodes mounted inside the selected blood vessel.

5. A method according to claim 1 wherein the device for generating the electric fields includes an induction coil that surrounds the selected blood vessel.

6. A method according to claim 1 wherein the electric signal has a wave form selected from the group consisting of an exponentially decaying pulse, a square pulse, a unipolar oscillating pulse train and a bipolar oscillating pulse train.

7. A method according to claim 1 wherein the electric fields have a strength of between approximately 0.2 kV/cm and 20.0 kV/cm.

8. A method according to claim 6 wherein each pulse has a duration of between approximately ten microseconds and one hundred milliseconds.

9. A method according to claim 6 wherein the electric fields apply between approximately one pulse and one hundred pulses to a given unit of liquid volume as the unit flows past the preselected location in the selected blood vessel.

10. A method according to claim 1 wherein the preselected cells are lymphocytes, the electric fields have a strength of approximately 0.55 kV/cm and the signal has a pulse train wave form that decays exponentially with a pulse duration of approximately fifty to fifty-five milliseconds.

11. An apparatus for introducing molecules in vivo into living blood cells of a patient, comprising:

an implantable electric field generating device sized and shaped to be implanted in the patient at a preselected location in close proximity of a selected blood stream and disposed at least partially around a center of a selected blood vessel through which the selected blood stream flows for generating electric fields at a preselected location within the selected blood vessel of the patient;

means for injecting a predetermined quantity of a fluid medium carrying preselected of said molecules into the selected blood vessel upstream of the preselected location within the selected blood vessel; and means for applying an electric signal to the implantable device for causing it to repeatedly generate electric fields of a predetermined amplitude and duration in order to make the walls of preselected cells in blood flowing past the preselected location within the selected blood vessel to be transiently permeable to permit the molecules to enter said preselected cells without killing said cells.

12. An apparatus according to claim 11 wherein the means for injecting the quantity of fluid carrying the molecules includes a pump.

13. An apparatus according to claim 11 wherein the means for applying an electric signal to the device includes a signal generator for generating the electric signal.

14. An apparatus according to claim 11 wherein the implantable device includes a pair of spaced apart conductive electrodes sized and shaped for implantation in the patient's body so that the blood in the selected blood vessel flows between the electrodes.

15. An apparatus according to claim 14 wherein the pair of conductive electrodes are sized and shaped for implantation in the selected blood vessel and coated with a clot inhibiting material with pores sufficiently large to permit ions to carry a charge between the electrodes.

16. An apparatus according to claim 15 wherein the implantable device further includes a dielectric cylinder surrounding and supporting the electrodes within the selected blood vessel.

17. An apparatus according to claim 16 wherein the electrodes are diametrically spaced apart so that the blood flows through the selected blood vessel.

18. An apparatus according to claim 16 wherein the electrodes are ring-shaped and are spaced apart.

19. An apparatus according to claim 11 wherein the implantable device is a coil sized and shaped for implantation in the patient and surrounding the selected blood vessel.

20. An apparatus according to claim 11 wherein the implantable device is a coil adapted for surrounding the blood vessel and has a serpentine configuration.

* * * * *